United States Patent [19]

Fischer, Sr. et al.

[11] Patent Number: 6,167,314
[45] Date of Patent: *Dec. 26, 2000

[54] CARDIAC PACEMAKER LEAD WITH PACEMAKER CONNECTOR

[75] Inventors: Elmar R. Fischer, Sr., Lake Jackson, Tex.; Hans Gerstmann, Lörrach, Germany

[73] Assignee: Intermedics Inc., Angleton, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 09/059,975

[22] Filed: Apr. 14, 1998

[51] Int. Cl.⁷ ..................................................... A61N 1/04
[52] U.S. Cl. ............................................................ 607/119
[58] Field of Search .................................... 607/115, 116, 607/119, 122; 600/372, 373, 374, 377; 439/909, 668

[56] References Cited

U.S. PATENT DOCUMENTS

| | | |
|---|---|---|
| 4,567,901 | 2/1986 | Harris . |
| 4,951,687 | 8/1990 | Ufford et al. ........................... 607/122 |
| 5,129,404 | 7/1992 | Spehr et al. . |
| 5,304,219 | 4/1994 | Chernoff et al. ........................ 607/122 |

FOREIGN PATENT DOCUMENTS 343402  11/1989  European Pat. Off. ................ 607/37

OTHER PUBLICATIONS

Intermedics Inc., Temporary Transcutaneous Pacing Wire Extension Lead Model 366–02—Sales Brochure, all pages, Oct. 1982.

*Primary Examiner*—George R. Evanisko
*Attorney, Agent, or Firm*—Schwegman, Lundberg, Woessner & Kluth, P.A.

[57] ABSTRACT

A cardiac stimulator lead connector is provided. The connector includes a pin member that has a distal end and a first insulating sleeve coupled to the pin member. An annular member is coupled to the first insulating sleeve. A conductor sleeve is coupled to the annular member and a second insulating sleeve is coupled to the conductor sleeve. One or more conductor wires running from distal electrodes in a lead may be welded to the connector. The connector eliminates crimping as a mechanism to secure lead conductors to lead connectors.

49 Claims, 3 Drawing Sheets

CARDIAC PACEMAKER LEAD WITH PACEMAKER CONNECTOR

BACKGROUND OF THE INVENTION

1. Field of the Invention

This invention relates generally to cardiac stimulator leads, and more particularly to a cardiac stimulator lead having a two-piece connector for connecting the lead to cardiac stimulator, such as a pacemaker or cardioverter/defibrillator.

2. Description of the Related Art

Conventional cardiac stimulator systems consist of a cardiac stimulator and an elongated flexible cardiac lead that is connected proximally to a header structure on the cardiac stimulator and is implanted distally at one or more sites within the heart requiring cardiac stimulation or sensing. The cardiac stimulator is normally a pacemaker, a cardioverter/defibrillator, a sensing instrument, or some combination of these devices.

At the time of implantation, the distal end of a cardiac lead is inserted through an incision in the chest and manipulated by the physician to the site requiring electrical stimulation with the aid of a flexible stylet that is removed prior to closure. At the site requiring electrical stimulation, the distal end of the lead is anchored to the endocardium by an active mechanism, such as a screw-in electrode tip, or alternatively, by a passive mechanism, such as one or more radially spaced tines that engage the endocardium. The proximal end of the lead is then connected to the cardiac stimulator and the incision is closed. The implantation route and site are usually imaged in real time by fluoroscopy to confirm proper manipulation and placement of the lead.

A conventional cardiac stimulator lead normally consists of an elongated flexible tubular, electrically insulating sleeve that is connected proximally to a connector that is adapted to couple to the header of a cardiac stimulator, and distally to a tubular tip electrode. One or more ring-type electrodes may be secured to the sleeve at various positions along the length of the sleeve. The proximal end of the lead sleeve is connected to the connector by application of various biocompatible adhesives to various portions of the connector and the sleeve. The tip electrode ordinarily consists of a tubular structure that has an increased diameter portion that forms an annular shoulder against which the distal end of the lead sleeve is abutted. The exterior surface of the tubular structure is normally smooth as is the interior surface of the distal end of the lead sleeve.

In many conventional cardiac stimulator leads, engagement between the one or more conductor wires of the lead and the connector is established by compressing the proximal ends of the wires between two concentrically positioned tubular structures. The compression is normally accomplished by crimping the outer of the two structures inward to compress the wire against the outer surface of the inner tubular structure. Establishment of the crimped connection involves aligning the cooperating tubular structures concentrically and longitudinally, feeding a sufficient portion of the conductor wire between the crimping tubular members, and crimping the tubular members to establish the crimped engagement.

There are several disadvantages associated with conventional lead connectors. Successful crimping of the cooperating tubular structures in the conventional connector requires special attention to be paid to dimensional tolerances and to the hardness of the materials used to fabricate the tubular structures. The load applied to crimp the tubular structures is based upon an expected hardness of the material as well as the design tolerance between the cooperating members. In circumstances where the tolerances between the cooperating tubular structures do not match design tolerances and/or the hardness of the tubular structures is greater than expected, the load applied may not be sufficient to successfully crimp and secure the conductor wire to the connector. As a result, the wire may make no or only intermittent electrical contact with the connector.

Verification testing of a conventional connector usually cannot identify a malfunction due to unsatisfactory crimping until the entire connector is fully assembled. This stems from the fact that the crimping step is one of the last steps in the assembly of a conventional connector. Since the crimping operation is not readily reversible, the ordinary remedy is to discard the malfunctioning connector. Aside from the material cost, another by-product of the inability to conduct interim verification test and/or visual inspection of the crimped connection is the costly expenditure of labor on a connector that is ultimately discarded.

Although a combination of crimping and adhesives is commonly employed to secure the proximal ends of a lead sleeve and the conductor wire(s) to the connector, the connection between the distal end of the lead sleeve and the tip electrode for most conventional cardiac leads is accomplished by use of an adhesive alone. A biocompatible adhesive, such as silicone based adhesive, is applied to the exterior of the tubular structure and the distal end of the lead sleeve is slipped over the tubular structure.

Many conventional lead designs incorporate a tip electrode that is composed of a non-radiopaque material. Although the motivations for selecting a non-radiopaque material for the tip electrode are several, a principle reason for selecting such materials is their ability to resist corrosion and maintain a relatively constant threshold voltage during long term exposure to the relatively hostile endocardial environment.

In addition to the aforementioned difficulties associated with conventional lead connectors, there are several other disadvantages associated with conventional designs for cardiac leads, and particularly the structure of the interface between the lead sleeve and the tip electrode. As noted above, a biocompatible adhesive is used as the dominant mechanism for securing the distal end of a lead sleeve to a tip electrode. To ensure that an adequate bond is formed between the adhesive and the mating surfaces of the lead sleeve and the tip electrode, most adhesives must be allowed to cure for durations of up to eight hours or more. This represents a significant bottle neck in the manufacturing and assembly process since the partially assembled lead must be set aside without further handling while the adhesive is allowed to cure.

Aside from manufacturing disadvantages, adhesives used for the sleeve-to-electrode joints may experience decreases in bond strength over time. The decrease may be caused by reactions with body fluids or tissues or may stem from inconsistent mixing and/or chemical makeup at the time of assembly. As a result, there exists a small risk that the lead sleeve may disconnect from the tip electrode in circumstances where an axial force is applied to the proximal end of the lead sleeve, such as when the lead is removed from the patient.

A lack of radiopacity is a shortcoming associated with conventional electrode tips that are composed of non-radiopaque material. Proper positioning of such leads is often a difficult task since the tips of such leads are not readily visible via fluoroscopy. In such circumstances, physicians often rely on the radiopaque character of the conducting coils inside the lead as an indicator of the position of the lead tip. However, for more modern leads incorporating individual small gage conductor wires, reliance upon the fluoroscopic visibility of the conductor wire may be insufficient as such fine wires normally do not show up clearly during fluoroscopy. A possible solution to the problem involves the incorporation of one or more radiographic markers into the lead sleeve. This technique involves additional expense and potentially complex manufacturing processes.

The present invention is directed to overcoming or reducing one or more of the foregoing disadvantages.

SUMMARY OF THE INVENTION

In accordance with one aspect of the present invention, a connector for a cardiac stimulator lead is provided. The connector includes a pin member that has a distal end and a first insulating sleeve coupled to the pin member. An annular member is coupled to the first insulating sleeve. A conductor sleeve is coupled to the annular member and a second insulating sleeve is coupled to the conductor sleeve.

In accordance with another aspect of the present invention, a connector for a cardiac stimulator lead is provided. The connector includes a pin member that has a tubular distal end. A first insulating sleeve is molded to the pin member. The first insulating sleeve has a first pair of external O-rings. An annular member is coupled to the first insulating sleeve. A conductor sleeve is coupled to the annular member. The conductor sleeve has a longitudinal bore for longitudinally receiving the annular member whereby the conductor sleeve abuts the first insulating sleeve. A second insulating sleeve is coupled to the conductor sleeve. The second insulating sleeve has a second pair of external O-rings.

In accordance with still another aspect of the present invention, a cardiac stimulator lead is provided. The lead includes a flexible tubular sleeve that has a first end and a second end. A tip electrode is coupled to the first end. A connector is coupled to the second end. The connector has a pin member that has a distal end, a first insulating sleeve coupled to the pin member, an annular member coupled to the first insulating sleeve, and a conductor sleeve coupled to the annular member. A second insulating sleeve is coupled to the conductor sleeve. A first conductor wire is coupled between the connector and the tip electrode.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
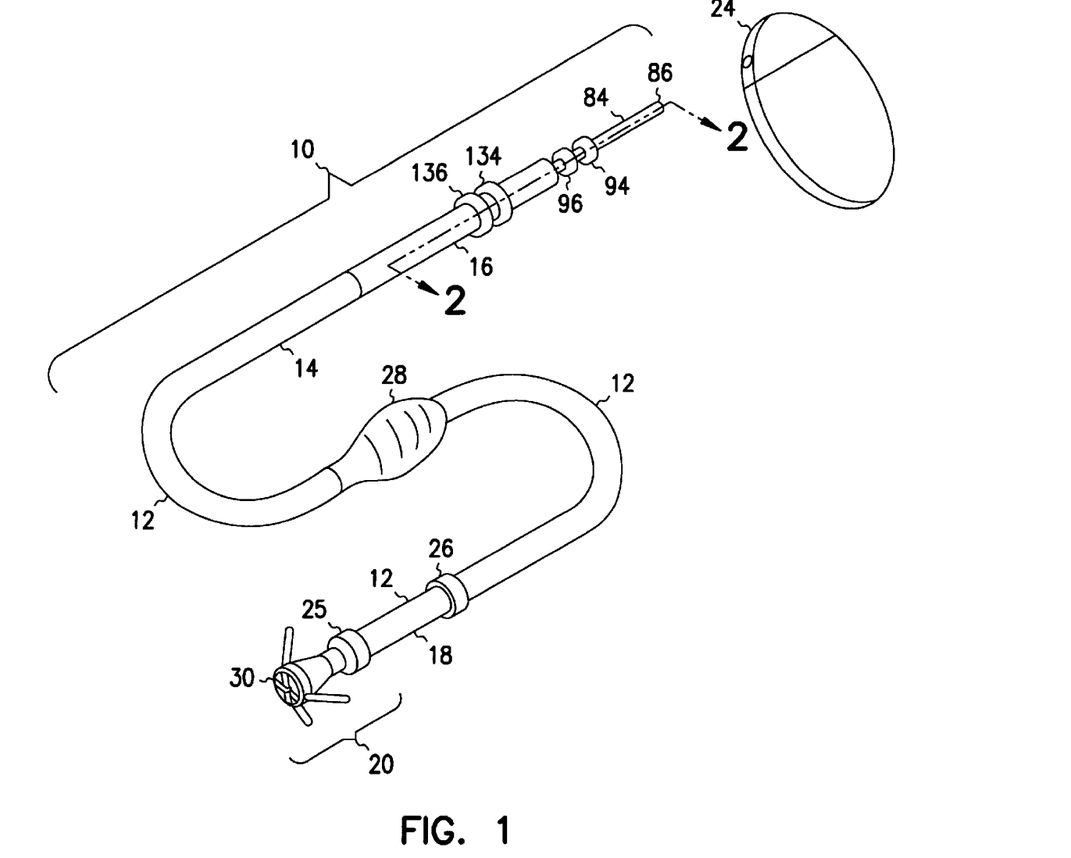
FIG. 1 is a pictorial view of an exemplary embodiment of a cardiac stimulator lead and a cardiac stimulator in accordance with the present invention.

In the drawings described below, reference numerals are generally repeated where identical elements appear in more than one figure. Turning now to the drawings, and in particular to FIG. 1, there is shown an exemplary cardiac lead 10 that includes a flexible insulating sleeve 12 that has a proximal end 14 coupled to a connector 16, and a distal end 18 coupled to a tip electrode assembly 20. The connector 16 is designed to be inserted into a cardiac stimulator 24, and is shown highly exaggerated in size relative to the cardiac stimulator 24. The cardiac stimulator 24 may be a pacemaker, a cardioverter/defibrillator, or other type of stimulator or a sensing instrument. The tip electrode assembly 20 includes an annular member to aid in securing the sleeve 12 to the electrode assembly 20 as described more fully below. The illustrated embodiment of the lead 10 is bipolar. Accordingly, the distal end 18 is provided with an electrode 26 located proximal to the tip electrode assembly 20. However, unipolar arrangements are possible as well. A suture sleeve 28 is slipped over the sleeve 12. During implantation, the suture sleeve 28 is sewn to body tissue at the site of transvenous entry.

The sleeve 12 is a flexible tubular member that provides a robust, electrically insulating coupling between the connector 16 (see FIG. 1) and the electrode assembly 20. The sleeve 12 protects one or more fine gage conductor wires enclosed therein from body fluids and tissues. The sleeve 12 is advantageously composed of a biocompatible, electrically insulating material, such as silicone, polyurethane, or like materials.

Figure 2:
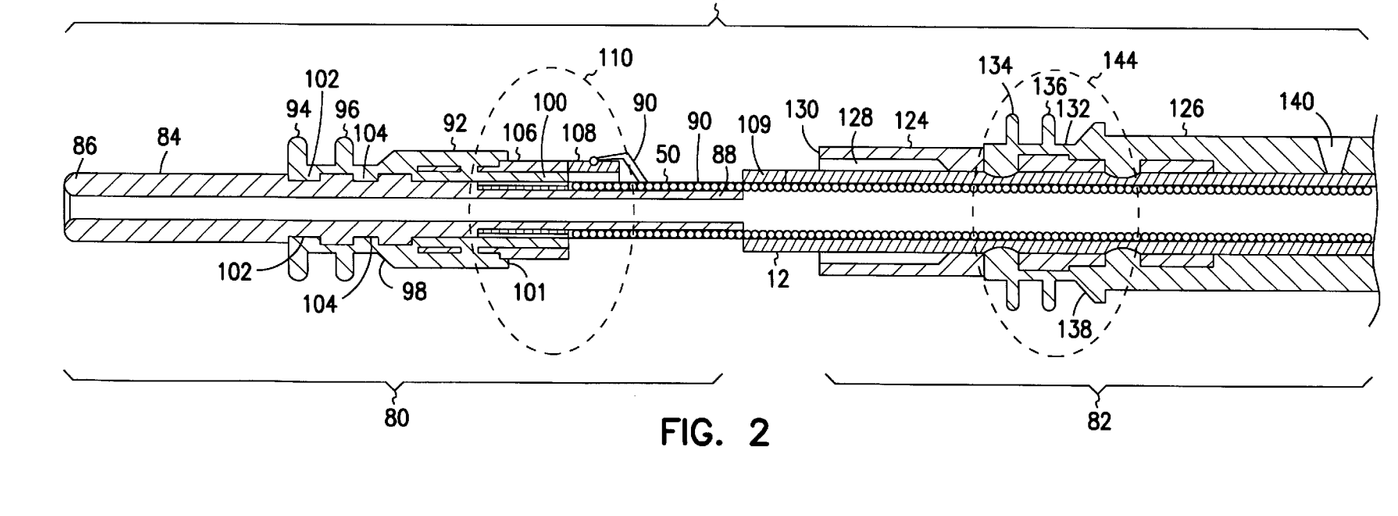
FIG. 2 is a cross-sectional view of FIG. 1 taken at section 2—2.

The detailed structure of the connector 16 may be understood by referring now to FIG. 2, which is a cross-sectional view of FIG. 1 taken at section 2—2. The connector 16 includes a connector pin assembly 80 coupled to a connector sleeve assembly 82. For clarity of illustration, the connector pin assembly 80 and the connector sleeve assembly 82 are shown exploded. The connector pin assembly 80 includes a tubular pin member 84 that has an elongated proximal end 86 designed to make electrical contact with one or more electrical contacts inside the cardiac stimulator 24 depicted in FIG. 1. The distal end 88 of the pin 84 is an elongated tubular member that is provided with an outer diameter suitable to accommodate the coils of a conductor wire 50 and a second conductor wire 90. The wire 50 is electrically connected distally to the electrode 30 depicted in FIG. 1, and the wire 90 is electrically connected distally to the annular electrode 26 depicted in FIG. 1. The connections of the wires 50 and 90 to the pin assembly 80 will be described in more detail below.

A first insulating sleeve 92 is coupled to the exterior of the pin member 84. The first insulating sleeve 92 includes longitudinally spaced apart O-rings 94 and 96 that are designed to engage structures within the cardiac stimulator 24 shown in FIG. 1 to provide a seal for the pin member 84 against the intrusion of body fluids following implantation. A single O-ring may be used in place of the pair. The first insulating sleeve 92 is provided with a proximally facing chamfer surface 98 that is principally designed to provide a tapered surface to facilitate easy insertion of the connector 16 into the cardiac stimulator 24 shown in FIG. 1. The first insulating sleeve 92 terminates distally in a reduced diameter portion 100. The reduction in diameter at the proximal end of the portion 100 defines a distally facing annular shoulder 101. The first insulating sleeve 92 is advantageously composed of a biocompatible flexible material that may be advantageously injection molded around the pin member 84. The material may be silicone, polyurethane, or like materials. In this way, the O-rings 94 and 96 may be formed integrally with the first insulating sleeve 92. Alternatively, the first insulating sleeve 92 may be provided with external grooves and the O-rings 94 and 96 secured to the first insulating sleeve 92 as separate members. To ensure a firm mechanical engagement between the first insulating sleeve 92 and the pin member 84, the pin member 84 is provided with two circumferential grooves 102 and 104 which fill with portions of the material used to form the first insulating sleeve 92 during the injection molding process. The number, shape, and spacing of the grooves, such as 102 and 104, is a matter of design discretion.

An annular member 106 is disposed around the reduced diameter portion 100. The annular member 106 includes a distally projecting flag 108 to which the conductor wire 90 is attached. The flag 108 is configured like a quarter cylindrical shell and is dimensioned with a large enough inner diameter to permit the conductor wires 50 and 90 to be spiraled around the distal end 88 and the sleeve 12 to be slipped over the wires 50 and 90 and abutted against the reduced diameter portion 100. The sleeve 12 is provided with a longitudinally extending slot 109 that is slightly wider than the outer diameter of the wire 90. The slot 109 provides a space to accommodate the wire 90 so that the sleeve 12 may be pushed past the wire 90 and abutted against the reduced diameter portion 100. It is desirable to electrically isolate the annular member 106 from the pin member 84 to alleviate the potential for short circuiting. This is particularly important during electrical verification testing, which is normally done at relatively high voltage. The primary electrical insulation is provided by the first insulating sleeve 92, and particularly the reduced diameter portion 100. In addition, the portions of the conductor wire 50 and the distal end 88 adjacent to the flag 108 may be encapsulated with a non-conducting epoxy.

Figure 3:
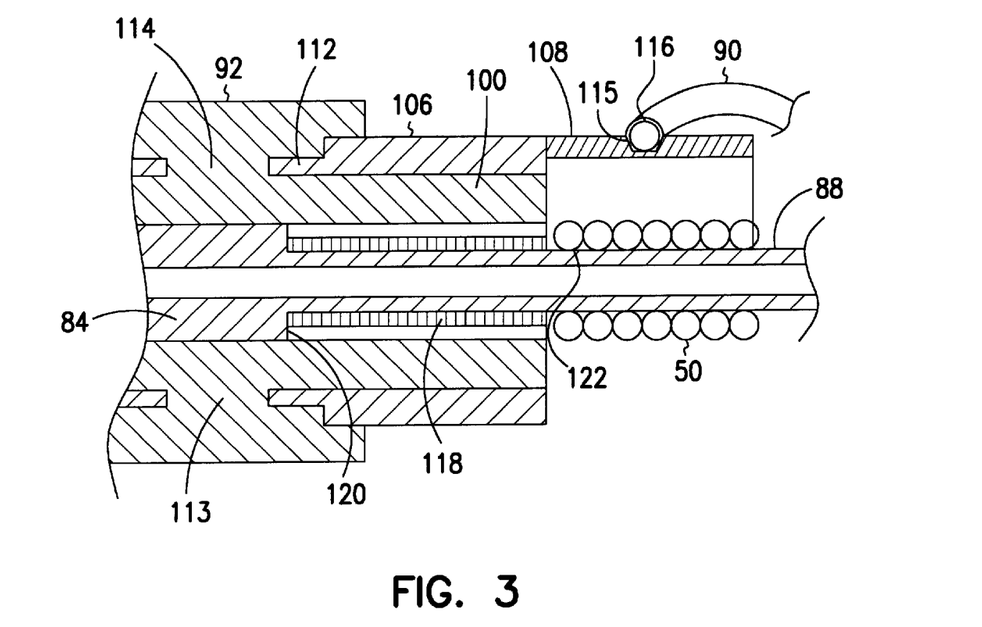
FIG. 3 is a detailed cross-sectional view of a designated portion of FIG. 2.

The details of the connections between the annular member 106 and the first insulating sleeve 92, and the respective connections between the conductor wires 50 and 90 and the annular member 106 and the pin member 84 may be understood by referring now to FIG. 3, which is a highly magnified view of the portion of FIG. 2 delineated by the dashed oval 110. The annular member 106 includes a proximally projecting reduced diameter nipple 112 that projects into the first insulating sleeve 92. The nipple has two or more circumferentially spaced ports 113 and 114 that enable molded structure to harden therein and provide a secure mechanical engagement between the first insulating sleeve 92 the annular member 106. The flag 108 is provided with an external circumferential groove 115 that is dimensioned to receive the stripped end 116 of the conductor wire 90. The stripped end 116 is secured to the flag 108 by laser welding or like welding techniques. The proximal end of the conductor wire 50 is stripped at 122 and the stripped end 122 is secured to the distal end 88 by laser welding or like welding techniques.

The embodiment depicted in FIGS. 2 and 3 is bipolar. However, a unipolar arrangement may be implemented by incorporating a single conductor wire, such as the wire 50, that is coupled to either the pin member 84 or to the annular member 106.

As noted above, one of the principle functions of the first insulating sleeve 92, and in particular the reduced diameter portion 100, is to electrically isolate the annular member 106 from the pin member 84, and in particular the distal end 88. Its anticipated that the material used to fabricate the first insulating sleeve 92 will readily fill the space, and provide a complete electrically insulating separation between the annular member 106 and the pin member 84. However, the skilled artisan will appreciate that there is the possibility of void formation during the molding process due to air bubbles or other mechanisms. If a void is formed in the reduced diameter portion 100 between the annular member 106 and the pin member 84, destructive arcing may occur in the void during high voltage electrical verification testing of the lead. To reduce the possibility of shorts through a void formed in the reduced diameter portion 100, an insulating annular member 118 may be slipped over the distal end 88 and abutted against the annular shoulder 120 of the pin member 84 prior to molding of the first insulating sleeve 92. The insulating annular member 118 may be composed of a variety of biocompatible insulating materials such as, for example, polyimide, polyurethane, or like materials.

Referring again to FIG. 2, the connector sleeve assembly 82 includes a conductor sleeve 124 that is coupled to a second insulating sleeve 126. The second insulating sleeve 126 is a tubular member of such length and the scale of FIG. 2 is such that the second insulating sleeve 126 is shown broken. The conductor sleeve 124 includes a proximally disposed bore 128 that is dimensioned so that the conductor sleeve 124 may be readily slipped over the annular member 106 until the annular surface 130 of the conductor sleeve 124 abuts the annular shoulder 101 of the first insulating sleeve 92. The conductor sleeve 124 is designed to establish an electrical pathway between the annular member 106 and a conducting structure inside the cardiac stimulator 24 shown in FIG. 1. Accordingly, the fit between the internal diameter of the conductor sleeve 124 and the outer diameter of the annular member 106 should be close enough to provide good electrical contact.

The proximal end 132 of the second insulating sleeve 126 is provided with two longitudinally spaced apart O-rings 134 and 136 that serve to seal the conductor sleeve 124 against the intrusion of body fluids. As with the aforementioned O-rings 94 and 96, the O-rings 134 and 136 may be integrally molded into the second insulating sleeve 126 or attached as separate members. On the distal side of the O-ring 136, the second insulating sleeve 126 expands in diameter and defines a chamfer surface 138 that provides the same functionality as the chamfer surface 98, albeit in conjunction with a different portion of the internal structure of the cardiac stimulator 24 shown in FIG. 1. The internal diameter of the second insulating sleeve 126 is generally dimensioned to provide a sliding fit with the outer surface of the sleeve 12 to permit easy assembly. The second insulating sleeve 126 is secured to the sleeve 12 by a suitable biocompatible medical grade adhesive, such as silicone, or any of a variety of two stage adhesives. To facilitate the introduction and spreading of the adhesive, the second insulating sleeve 126 is provided with a port 140. Adhesive is introduced into the port 140 under slight pressure to encourage the rapid and uniform spreading of the adhesive around the sleeve 12. The flow characteristics of the adhesive may be enhanced by thinning with a suitable diluent, such as heptane, prior to injection through the port 140. In addition, adhesive is back filled between the second insulating sleeve 126 and the sleeve 12 by injection under slight pressure at the interface designated 142.

Figure 4:
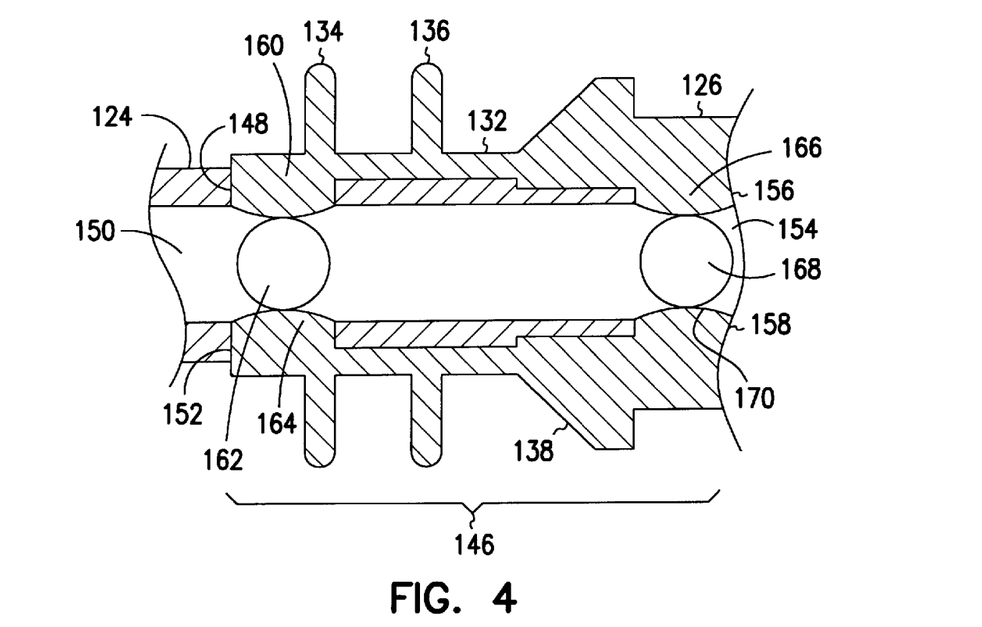
FIG. 4 is a detailed cross-sectional view of another designated portion of FIG. 2.

The connection between the conductor sleeve 124 and the second insulating sleeve 126 may be more readily understood by referring now to FIG. 4, which is a magnified view of the portion of FIG. 2 circumscribed by the dashed oval 144. Note that in FIG. 4, the sleeve 12 is not shown for clarity of illustration. A central portion 146 of the conductor sleeve 124 is provided with a plurality of circumferentially spaced bores, six of which are depicted at 148, 150, 152, 154, 156, and 158. The bores 148, 150, 152, 154, 156, and 158 are designed to enable the material used to mold the second insulating sleeve 126 to flow into the bores 148, 150, 152, 154, 156, and 158 and harden into buttons 160, 162, 164, 166, 168, and 170. The engagement between the buttons 160, 162, 164, 166, 168, and 170 and the central portion 146 of the conductor sleeve 124 establishes a secure mechanical engagement between the conductor sleeve 124 and the second insulating sleeve 126. The second insulating sleeve 126 is advantageously composed of the same types of materials used to fabricate the first insulating sleeve 92 shown in FIGS. 2 and 3, and is advantageously injection molded.

The pin member 84, the annular member 106, and the conductor sleeve 124 are advantageously composed of a biocompatible conducting material that may be welded via laser or like techniques. Exemplary materials include 316L stainless steel, other suitable types of stainless steel, MP35N, or like materials.

The connector 16 depicted in FIGS. 1, 2, 3, and 4, eliminates the necessity for one or more tubular crimping members and the attendant difficulties in establishing consistent and reliable crimped connections between the conductor wires of the lead and the various crimping members. Reliable electrical and mechanical connection between the conductor wires 50 and 90 and the connector 16 are established by welding. The use of welded connections in lieu of crimping tubes or slugs permits interim inspection and testing of the wire-to-connector connections and more rapid assembly.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A connector for a cardiac stimulator lead, comprising:
   a pin member having a distal end;
   a first insulating sleeve coupled to the pin member;
   an annular member coupled to the first insulating sleeve;
   a conductor sleeve coupled to the annular member;
   a second insulating sleeve coupled to the conductor sleeve; and
   a preformed insulative annular member between the first insulating sleeve and the pin member, wherein the preformed insulative annular member, the first insulating sleeve, and the pin member are in a fixed relation to one another.

2. The connector of claim 1, wherein the first insulating sleeve is coupled to the pin member by a first molding process and the second insulating sleeve is coupled to the conductor sleeve by a second molding process.

3. The connector of claim 1, wherein the first insulating sleeve has a first pair of external O-rings and the second insulating sleeve has a second pair of external O-rings.

4. The connector of claim 3, wherein the first pair of external O-rings being integrally molded with the first insulating sleeve and the second pair of external O-rings being integrally molded with the second insulating sleeve.

5. The connector of claim 1, wherein the conductor sleeve is welded to the annular member.

6. The connector of claim 1, wherein the annular member has a longitudinally projecting flag for coupling to a conductor wire of the lead.

7. The connector of claim 1, wherein the distal end of the pin member comprises an elongated tubular member.

8. The connector of claim 1, wherein the preformed insulative annular member is disposed between the distal end and the annular member and is coupled to the distal end.

9. The connector of claim 1, wherein the conductor sleeve has a longitudinal bore for longitudinally receiving the annular member and wherein the conductor sleeve abuts the first insulating sleeve.

10. The connector of claim 9, further comprising a first pair of external O-rings being integrally molded with the first insulating sleeve and a second pair of external O-rings being integrally molded with the second insulating sleeve.

11. The connector of claim 9, wherein the conductor sleeve is welded to the annular member.

12. The connector of claim 9, wherein the annular member has a longitudinally projecting flag for coupling to a conductor wire of the lead.

13. The connector of claim 9, wherein the insulative annular member is disposed between the distal end and the annular member and is coupled to the distal end.

14. A cardiac stimulator lead, comprising:
   a flexible tubular sleeve having a first end and a second end;
   a tip electrode coupled to the first end;
   a connector coupled to the second end, the connector having a pin member having a distal end, a first insulating sleeve coupled to the pin member, an annular member coupled to the first insulating sleeve, and a conductor sleeve coupled to the annular member; and a preformed insulative annular member between the first insulating sleeve and the pin member, wherein the preformed insulative annular member, the first insulating sleeve, and the pin member are in a fixed relation to one another;
   a second insulating sleeve coupled to the conductor sleeve; and
   a first conductor wire coupled between the connector and the tip electrode.

15. The cardiac stimulator lead of claim 14, wherein the first conductor wire is welded to the pin member.

16. The cardiac stimulator lead of claim 15, further comprising a second electrode coupled to the tubular sleeve and a second conductor wire coupled between the second electrode and the annular member.

17. The cardiac stimulator lead of claim 16, wherein the annular member has a longitudinally projecting flag and the second conductor wire is welded to the flag.

18. The cardiac stimulator lead of claim 14, wherein the first insulating sleeve is coupled to the pin member by a first molding process and the second insulating sleeve is coupled to the conductor sleeve by a second molding process.

19. The cardiac stimulator lead of claim 14, wherein the first insulating sleeve has a first pair of external O-rings and the second insulating sleeve has a second pair of external O-rings.

20. The cardiac stimulator lead of claim 19, wherein the first pair of external O-rings being integrally molded with the first insulating sleeve and the second pair of external O-rings being integrally molded with the second insulating sleeve.

21. The cardiac stimulator lead of claim 14, wherein the conductor sleeve is welded to the annular member.

22. The cardiac stimulator lead connector of claim 14, wherein the preformed insulative annular member is disposed between the distal end and the annular member and is coupled to the distal end.

23. A connector for a cardiac stimulator lead, comprising:

a pin member having a distal end;

a first insulating sleeve coupled to the pin member;

an annular member coupled to the first insulating sleeve, the annular member including a longitudinally projecting flag for coupling to a conductor wire of the lead;

a conductor sleeve coupled to the annular member; and a second insulating sleeve coupled to the conductor sleeve.

24. A connector for a cardiac stimulator lead, comprising:

a pin member having a tubular distal end;

a first insulating sleeve molded around the pin member, the first insulating sleeve having a first pair of external O-rings, the first pair of external O-rings being integrally molded with the first insulating sleeve;

an annular member coupled to the first insulating sleeve, the annular member having a longitudinally projecting flag for coupling to a conductor wire of the lead;

a conductor sleeve coupled to the annular member, the conductor sleeve having a longitudinal bore for longitudinally receiving the annular member whereby the conductor sleeve abuts the first insulating sleeve; and a second insulating sleeve coupled to the conductor sleeve, the second insulating sleeve having a second pair of external O-rings, the second pair of external O-rings being integrally molded with the second insulating sleeve.

25. A cardiac stimulator lead, comprising:

a flexible tubular sleeve having a first end and a second end;

a tip electrode coupled to the first end;

a second electrode coupled to the tubular sleeve;

a connector coupled to the second end, the connector having:

a pin member having a distal end;

a first insulating sleeve coupled to the pin member;

an annular member coupled to the first insulating sleeve, the annular member having a longitudinally projecting flag; and a conductor sleeve coupled to the annular member;

a second insulating sleeve coupled to the conductor sleeve;

a first conductor wire coupled between the connector and the tip electrode, wherein the first conductor wire is welded to the pin member; and a second conductor wire coupled between the annular member and the second electrode, wherein the second conductor wire is welded to the longitudinally projecting flag of the annular member.

26. A connector adapted for mating to conducting structure inside a cardiac stimulator, comprising:

a connector pin assembly including:

a pin member having a distal end;

a first insulating sleeve coupled to the pin member; and an annular member coupled to the first insulating sleeve;

a connector sleeve assembly including:

a conductor sleeve adapted for providing an electrical pathway between the annular member and the conducting structure inside the cardiac stimulator, the conductor sleeve having at least one bore; and a second insulating sleeve coupled to the conductor sleeve, the second insulating sleeve having a portion molded through the at least one bore wherein the portion of the mold forms a button for securing the second insulating sleeve to the conductor sleeve.

27. The connector of claim 26 further comprising:

the first insulating sleeve having a first pair of integrally molded external O-rings;

the second insulating sleeve having a second pair of integrally molded external O-rings.

28. The connector of claim 26, further comprising:

a flexible tubular sleeve having a first end and a second end;

a tip electrode coupled to the first end;

an annular electrode coupled to proximal the first end;

wherein one or more buttons of the second insulating sleeve secure the conductor sleeve to the second insulating sleeve;

a first conductor wire coupled between the pin and the tip electrode;

a second conductor wire coupled between the annular member and the annular electrode.

29. A connector for a cardiac stimulator lead, comprising:

a pin member having a distal end;

an annular member having at least one port;

a first insulating sleeve molded to the pin member and having one or more portions molded through the at least one port for securing the first insulating sleeve to the annular member, wherein the pin member, the annular member and the first insulating sleeve are in fixed relation to one another;

a conductor sleeve; and a second insulating sleeve molded to the conductor sleeve, wherein the conductor sleeve and the second insulating sleeve are in fixed relation to one another, the conductor sleeve longitudinally engaged over the annular member.

30. The connector of claim 29 wherein the first insulating sleeve includes a chamfer surface.

31. The connector of claim 29 wherein the second insulating sleeve includes a chamfer surface.

32. The connector of claim 29 wherein the second insulating sleeve includes a port for injecting adhesive between the second insulating sleeve and a sleeve of the cardiac stimulator lead.

33. The connector of claim 29 wherein the pin member having a proximal end for contacting a conducting structure inside a cardiac stimulator and the pin member having one or more grooves;

the annular member having:

an external surface;

the annular member positioned around a portion of the pin member wherein a gap remains between the pin member and annular member;

the first insulating sleeve molded around the external surface of the annular member and through the at least one port of the annular member and filling the gap and filling the one or more grooves; and the conductor sleeve having:

a proximal portion having an internal bore for slidably engaging the distal portion of the annular member wherein conductive contact is established between the conductor sleeve and the annular member;

a distal portion having an inner diameter capable of sliding over a sleeve of a lead and having at least one bore;

the second insulating sleeve having:

a proximal portion molded around the distal portion of the conductor sleeve and through the at least one bore wherein a portion of the mold forms a button for securing the second insulating sleeve to the conductor sleeve; and a distal portion having an inner diameter capable of sliding over a sleeve of the cardiac stimulator lead.

34. A connector for a cardiac stimulator lead, comprising:

a pin member having a distal end;

a first insulating sleeve coupled to the pin member;

an annular member coupled to the first insulating sleeve;

a conductor sleeve coupled to the annular member;

a second insulating sleeve coupled to the conductor sleeve; and a preformed insulative annular member between the first insulating sleeve and the pin member;

wherein the annular member has a longitudinally projecting flag for coupling to a conductor wire of the lead.

35. The connector of claim 34, wherein the first insulating sleeve has a first pair of external O-rings and the second insulating sleeve has a second pair of external O-rings.

36. The connector of claim 35, wherein the first pair of external O-rings being integrally molded with the first insulating sleeve and the second pair of external O-rings being integrally molded with the second insulating sleeve.

37. The connector of claim 34, wherein the conductor sleeve is welded to the annular member.

38. The connector of claim 34, wherein the conductor sleeve has a longitudinal bore for longitudinally receiving the annular member and wherein the conductor sleeve abuts the first insulating sleeve.

39. A connector for a cardiac stimulator lead, comprising:

a pin member having a distal end;

a first insulating sleeve coupled to the pin member;

an annular member coupled to the first insulating sleeve;

a conductor sleeve coupled to the annular member;

a second insulating sleeve coupled to the conductor sleeve; and a preformed insulative annular member between the first insulating sleeve and the pin member;

wherein the conductor sleeve has a longitudinal bore for longitudinally receiving the annular member and wherein the conductor sleeve abuts the first insulating sleeve;

wherein the annular member has a longitudinally projecting flag for coupling to a conductor wire of the lead.

40. The connector of claim 39, wherein the first insulating sleeve has a first pair of external O-rings and the second insulating sleeve has a second pair of external O-rings.

41. The connector of claim 39, wherein the conductor sleeve is welded to the annular member.

42. A cardiac stimulator lead, comprising:

a flexible tubular sleeve having a first end and a second end;

a tip electrode coupled to the first end;

a connector coupled to the second end, the connector having a pin member having a distal end, a first insulating sleeve coupled to the pin member, an annular member coupled to the first insulating sleeve, and a conductor sleeve coupled to the annular member; and a preformed insulative annular member between the first insulating sleeve and the pin member;

a second insulating sleeve coupled to the conductor sleeve;

a first conductor wire welded to the pin member and coupled between the connector and the tip electrode; and a second electrode coupled to the tubular sleeve and a second conductor wire coupled between the second electrode and the annular member;

wherein the annular member has a longitudinally projecting flag and the second conductor wire is welded to the flag.

43. The cardiac stimulator lead of claim 42, wherein the first insulating sleeve has a first pair of external O-rings and the second insulating sleeve has a second pair of external O-rings.

44. The cardiac stimulator lead of claim 43, wherein the first pair of external O-rings being integrally molded with the first insulating sleeve and the second pair of external O-rings being integrally molded with the second insulating sleeve.

45. The cardiac stimulator lead of claim 42, wherein the conductor sleeve is welded to the annular member.

46. A connector for a cardiac stimulator lead, comprising:

a pin member having a distal end;

an annular member;

a first insulating sleeve molded to the pin member and the annular member, wherein the pin member, the annular member and the first insulating sleeve are in fixed relation to one another;

a conductor sleeve; and a second insulating sleeve molded to the conductor sleeve, wherein the conductor sleeve and the second insulating sleeve are in fixed relation to one another, the conductor sleeve longitudinally engaged over the annular member;

wherein the pin member having a proximal end for contacting a conducting structure inside a cardiac stimulator and the pin member having one or more grooves;

the annular member having:

an external surface;

a proximal portion having at least one port, the annular member positioned around a portion of the pin member wherein a gap remains between the pin member and annular member;

the first insulating sleeve molded around the proximal portion of the external surface of the annular member and through the port of the annular member and filling the gap and filling the grooves; and the conductor sleeve having:

a proximal portion having an internal bore for slidably engaging a distal portion of the annular member wherein conductive contact is established between the conductor sleeve and the annular member;

a distal portion having an inner diameter capable of sliding over a sleeve of a lead and having at least one bore;

the second insulating sleeve having:

a proximal portion molded around the distal portion of the conductor sleeve and through the at least one bore wherein a portion of the mold forms a button for securing the second insulating sleeve to the conductor sleeve; and a distal portion having an inner diameter capable of sliding over a sleeve of the cardiac stimulator lead.

47. The connector of claim 46, wherein the first insulating sleeve includes a chamfer surface.

48. The connector of claim 46, wherein the second insulating sleeve includes a chamfer surface.

49. The connector of claim 46 wherein the second insulating sleeve includes a port for injecting adhesive between the second insulating sleeve and a sleeve of the cardiac stimulator lead.

* * * * *